US012612590B2

(12) United States Patent
Makino et al.

(10) Patent No.: US 12,612,590 B2
(45) Date of Patent: Apr. 28, 2026

(54) CELL CULTURE EVALUATION SYSTEM

(71) Applicants:Nihon Kohden Corporation, Tokyo (JP); Osaka University, Osaka (JP)

(72) Inventors: Hodaka Makino, Tokorozawa (JP); Hirotsugu Kubo, Tokorozawa (JP); Masahiro Kinooka, Suita (JP)

(73) Assignees: Nihon Kohden Corporation, Tokyo (JP); Osaka University, Osaka (JP)

( * ) Notice: Subject to any disclaimer, the term of this patent is extended or adjusted under 35 U.S.C. 154(b) by 961 days.

(21) Appl. No.: 17/788,269

(22) PCT Filed: Dec. 21, 2020

(86) PCT No.: PCT/JP2020/047754
§ 371 (c)(1),
(2) Date: Jun. 22, 2022

(87) PCT Pub. No.: WO2021/132185
PCT Pub. Date: Jul. 1, 2021

(65) Prior Publication Data
US 2023/0035766 A1　Feb. 2, 2023

(30) Foreign Application Priority Data
Dec. 24, 2019　(JP) ................................. 2019-233044

(51) Int. Cl.
*C12M 1/34*　(2006.01)
*C12M 1/36*　(2006.01)
(52) U.S. Cl.
CPC .............. *C12M 41/36* (2013.01); *C12M 1/34* (2013.01); *C12M 41/12* (2013.01); *C12M 41/48* (2013.01)

(58) Field of Classification Search
None
See application file for complete search history.

(56) References Cited

U.S. PATENT DOCUMENTS

2013/0027539 A1*　1/2013　Kiyota ................... C12M 41/36
　　　　　　　　　　　　　　　　348/79
2013/0260445 A1　10/2013　Oura et al.
(Continued)

FOREIGN PATENT DOCUMENTS

JP　　　2013202030 A　10/2013
JP　　　2016508610 A　3/2016
(Continued)

OTHER PUBLICATIONS

International Search Report and Written Opinion received for International Application No. PCT/JP2020/047754, mailed on Mar. 31, 2021, 8 pages.
(Continued)

*Primary Examiner* — Holly Kipouros
(74) *Attorney, Agent, or Firm* — Dorsey & Whitney LLP

(57) ABSTRACT

The presently disclosed subject matter provides a cell culture evaluation system including a measurement unit, a first storage unit, a second storage unit, an evaluation unit and an output unit, wherein the measurement unit includes a sensor that acquires evaluation target data about motion or a state of a culture tool; the first storage unit stores the evaluation target data; the second storage unit stores reference (tion unit compares the evaluation target data with the reference data so as to evaluate an execution state of a cell culture process; and the output unit outputs an evaluation result created by the evaluation unit.

17 Claims, 6 Drawing Sheets

(56) References Cited

U.S. PATENT DOCUMENTS

| | | | |
|---|---|---|---|
| 2017/0166948 A1 | 6/2017 | Matsumoto | |
| 2017/0227564 A1* | 8/2017 | Muschler | ........... G01B 11/0608 |
| 2018/0330510 A1 | 11/2018 | Watanabe | |
| 2019/0010441 A1* | 1/2019 | Kindaichi | ............. C12M 23/50 |
| 2020/0110922 A1 | 4/2020 | Shinoda | |

FOREIGN PATENT DOCUMENTS

| | | | |
|---|---|---|---|
| JP | 2017092730 A | 5/2017 |
| WO | 2014127285 A1 | 8/2014 |
| WO | 2016039010 A1 | 3/2016 |
| WO | 2016132398 A1 | 8/2016 |
| WO | 2017082167 A1 | 5/2017 |
| WO | 2018230178 A1 | 12/2018 |
| WO | 2021132185 A1 | 7/2021 |

OTHER PUBLICATIONS

Hotaka, "Quantitative Evaluation of Cell Culture Operation Using Accelerometer", Medical Device Science, vol. 85, No. 4, 2015, pp. 438-442 (6 pages of English translation included).

Kato, "Development of Image-Based Informatics as Non-Invasive Quality Control Technology for Controlling Regenerative Medicine Product", Journal of Biological Engineering vol. 96, No. 3, pp. 121-128, 2018 (14 pages of English translation included).

Office Action issued in Japanese Patent Application No. 2019-233044, mailed on Dec. 19, 2023, 12 pages including 6 pages of English translation.

* cited by examiner

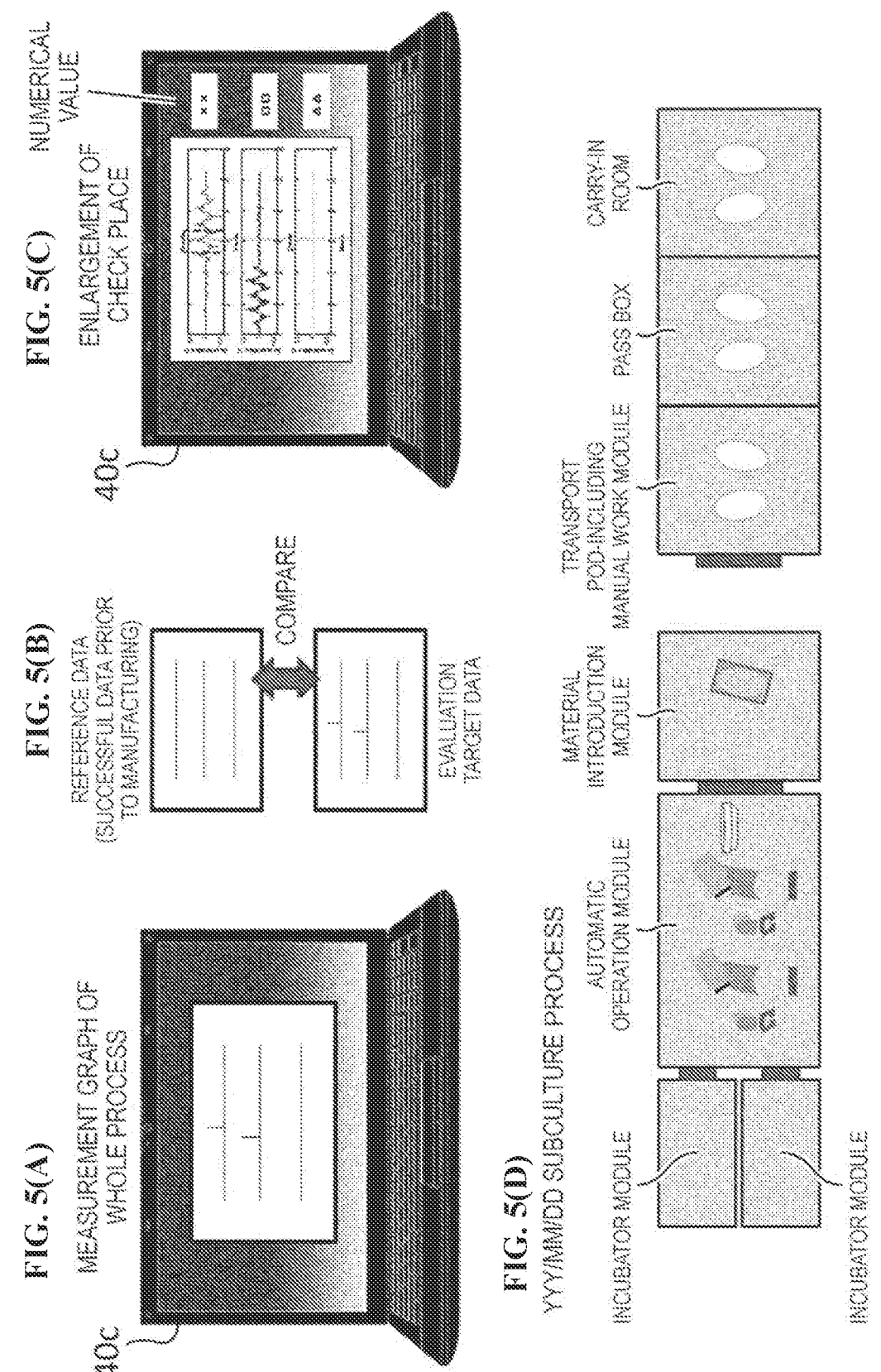

FIG. 5(A)
MEASUREMENT GRAPH OF WHOLE PROCESS
40c

FIG. 5(B)
REFERENCE DATA (SUCCESSFUL DATA PRIOR TO MANUFACTURING)
COMPARE
EVALUATION TARGET DATA

FIG. 5(C)
ENLARGEMENT OF CHECK PLACE
NUMERICAL VALUE
40c

FIG. 5(D)
YYY/MM/DD SUBCULTURE PROCESS
INCUBATOR MODULE
AUTOMATIC OPERATION MODULE
MATERIAL INTRODUCTION MODULE
TRANSPORT POD-INCLUDING MANUAL WORK MODULE
PASS BOX
CARRY-IN ROOM
INCUBATOR MODULE

1

CELL CULTURE EVALUATION SYSTEM

TECHNICAL FIELD

This application is 371 of International Patent Application PCT/JP2020/047754 filed on Dec. 21, 2020 which in turn claims priority to Japanese Patent Application No. 2019-233044 filed on Dec. 24, 2017, the entire content of which are incorporated herein by reference.

BACKGROUND ART

Cells used for generative medicine or cells used for manufacturing biomedicine or the like are required to be incubated for a long period of time while being kept in a sterile environment. However, the nature or the state of the cells varies due to a culture condition, the kind of a cell line, etc. In some cases, the cells cannot be obtained with a desired quality. In order to produce a large quantity of cells keeping the desired quality, the cells are required to be incubated while the culture condition is kept constant. Various cell culture apparatuses for attaining this requirement have been developed.

In a facility manufacturing cells, culture apparatuses are used in combination in accordance with an application so as to manufacture the cells. In a case where cells which are difficult to be processed by the culture apparatuses are used, the cells are manufactured by manual work processes used in combination. As described above, even a slight difference of a culture process may however affect the nature or the state of the cells. In order to manufacture a cell product keeping a fixed quality, training workers to be skillful, or development of an automatic culture apparatus which can surely execute a culture operation as well as a skillful worker are essential.

Experiments for quantitatively evaluating culture operations executed by workers or by automatic culture apparatuses have been performed, and culture state monitoring systems have been therefore developed (PTL 1, NPL 1 and NPL 2).

CITATION LIST

Patent Literature

PTL 1: JP-A-2013-202030

Non Patent Literature

NPL 1: Makino Hotaka, Quantitative Evaluation of Cell Culture Operation Using Accelerometer, The Japanese Journal of Medical Instrumentation, 85(4), 438-442, 2015
NPL 2: Kato Ryuji, Development of Image-based Informatics as Non-invasive Quality Control Technology for Controlling Regenerative Medicine Product, Seibutsu-kogaku Kaishi, 96(3), 121-128, 2018

SUMMARY OF INVENTION

Technical Problem

It is difficult to perform destructive inspection on a cell product due to the nature of the cell product. Therefore, processes described in a standard operation procedure (SOP) are executed strictly so as to assure the quality of the final product. However, even when the work processes have been executed faithfully, the quality of the manufactured final cell product still varies due to a difference in skill level of culture operation between workers or a difference in motion between culture apparatuses. Since only inspection tasks of items determined by each use facility and each culture apparatus maker are performed in periodic inspection to check the motion of the culture apparatus, it is necessary to check whether a desired culture operation can be performed or not as the whole of a culture process.

Solution to Problem

As a result of keen examination which has been made by the present inventors, a system which can evaluate processes of manufacturing a cell product has been developed to solve the foregoing problem. That is, the presently disclosed subject matter includes the following items.

[1] A cell culture evaluation system including a measurement unit, a first storage unit, a second storage unit, an evaluation unit, and an output unit, wherein:
    the measurement unit includes a sensor that acquires evaluation target data about motion or a state of a culture tool in execution of an arbitrary culture process;
    the first storage unit stores the evaluation target data;
    the second storage unit stores reference data about reference motion or a reference state of the culture tool in execution of a referred culture process;
    the evaluation unit compares the evaluation target data stored in the first storage unit with the reference data stored in the second storage unit so as to evaluate an execution state of a cell culture process;
    the output unit outputs an evaluation result created by the evaluation unit; and the culture tool includes a culture container, and a pipette and/or a centrifuge tube.

[2] The cell culture evaluation system according to Item 1, wherein:
    each of the evaluation target data and the reference data include at least one selected from the group consisting of acceleration, angular velocity, position, posture, an operating time, the number of times of use, and temperature of the culture tool, and an amount of a liquid contained in the culture tool, dissolved oxygen (DO) in the liquid, turbidity, a discharge flowrate, a suction flowrate and pH.

[3] The cell culture evaluation system according to Item 1 or 2, wherein:
    the evaluation unit compares the evaluation target data stored in the first storage unit with the reference data stored in the second storage unit, and evaluates the execution of the cell culture process as abnormal at an arbitrary time point when the evaluation target data at the arbitrary time point deviate from a predetermined condition set by the reference data at a corresponding time point to the arbitrary time point; and
    the output unit outputs an evaluation result including information about the time point at which the abnormality occurred.

[4] The cell culture evaluation system according to any one of Items 1 to 3, wherein:
    the output unit outputs the evaluation result as a time-series trend graph of the evaluation target data and the reference data.

[5] The cell culture evaluation system according to Item 4, wherein:
    the trend graph can be enlarged and decreased by any scale factor.

[6] The cell culture evaluation system according to Item 3, wherein:

the output unit outputs the evaluation target data and the reference data as a time-series trend graph, and displays the information about the time point at which the execution of the cell culture process was evaluated as abnormal on the trend graph.

[7] The cell culture evaluation system according to any one of Items 1 to 6, wherein:

the measurement unit includes a third storage unit that stores the evaluation target data, and the evaluation target data stored in the third storage unit are transferred to the first storage unit to be used.

[8] The cell culture evaluation system according to any one of Items 1 to 7, wherein:

the first storage unit is a portable type storage device.

[9] The cell culture evaluation system according to any one of Items 1 to 8, wherein:

the measurement unit includes a first transmission unit that transmits the evaluation target data; and the first storage unit receives the evaluation target data transmitted from the first transmission unit through a first reception unit, and stores the received evaluation target data.

[10] The cell culture evaluation system according to any one of Items 1 to 9, wherein:

the cell culture evaluation system further comprises a sensor control unit that issues an instruction for controlling start and stop of motion of the measurement unit, and a second transmission unit that transmits the instruction; and the measurement unit further includes a second reception unit that receives the instruction transmitted from the second transmission unit.

[11] The cell culture evaluation system according to any one of Items 1 to 10, wherein:

the cell culture evaluation system further comprises a third transmission unit that transmits a parameter about a measurement condition of motion of a sensor included in the measurement unit; and the measurement unit further includes a third reception unit that receives the parameter transmitted from the third transmission unit.

[12] The cell culture evaluation system according to any one of Items 1 to 11, further comprising an imaging unit and a fourth storage unit, wherein:

the imaging unit acquires an evaluation target image about motion or a state of the culture tool in execution of the arbitrary culture process;

the second storage unit stores a reference image about the reference motion or the reference state of the culture tool in execution of the referred culture process; the fourth storage unit stores the evaluation target image; and the output unit outputs the reference image and/or the evaluation target image in association with the evaluation result if occasions demand.

[13] The cell culture evaluation system according to Item 12, wherein:

the imaging unit includes a fifth storage unit that stores the evaluation target image, and the evaluation target image stored in the fifth storage unit is transferred to the fourth storage unit to be used.

[14] The cell culture evaluation system according to Item 12 or 13, wherein:

the fourth storage unit is a portable type storage device.

[15] The cell culture evaluation system according to any one of Items 12 to 14, wherein:

the imaging unit includes a fourth transmission unit that transmits the evaluation target image; and the fourth storage unit receives the evaluation target image transmitted from the fourth transmission unit through a fourth reception unit, and stores the received evaluation subject image.

[16] The cell culture evaluation system according to any one of Items 1 to 15, wherein:

the cell culture evaluation system evaluates a culture process carried out by a person or an automatic culture apparatus.

[17] The cell culture evaluation system according to any one of Items 1 to 15, wherein:

the second storage unit stores a layout of the culture tool and a culture material on a time-series basis in execution of the referred culture process; and the output unit outputs the evaluation result associated with the layout.

Advantageous Effects of Invention

According to the presently disclosed subject matter, motion or a condition in a cell culture process carried out by a worker and/or a cell culture apparatus can be evaluated quantitatively, and the motion or the condition which may affect the quality of cells can be analyzed. In addition, by use of the presently disclosed subject matter, the quality of a final cell product can be assured.

BRIEF DESCRIPTION OF DRAWINGS

FIGS. 5 (A) to (D) illustrate examples of images displayed on an output unit of a corresponding one of the cell culture evaluation systems according to each of the embodiments.

DESCRIPTION OF EMBODIMENTS

Figure 1:
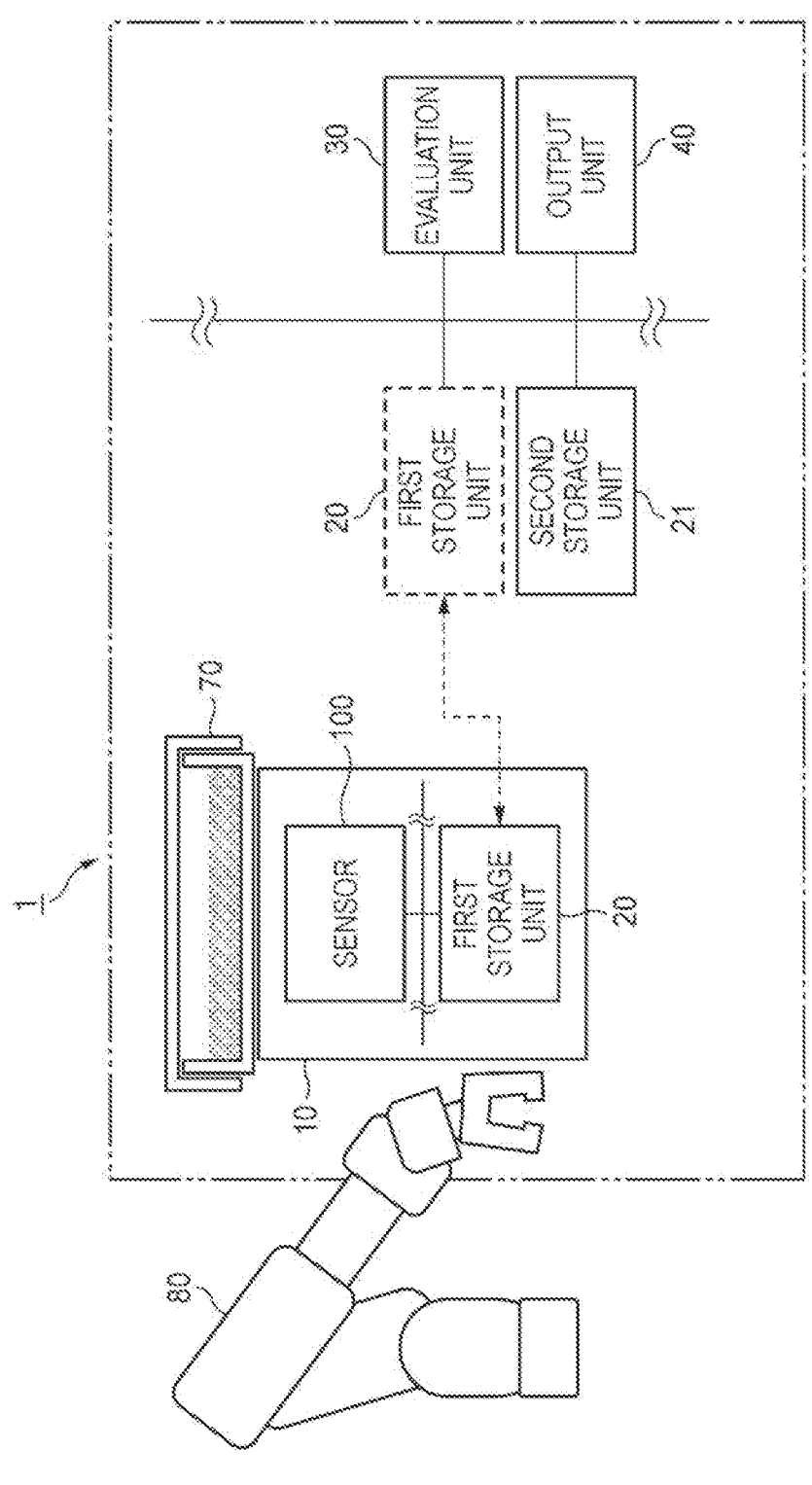
FIG. 1 is a schematic configuration view of a cell culture evaluation system according to an embodiment.

The presently disclosed subject matter will be described below through embodiments of the subject matter while referring to the drawings if occasions demand. The following embodiments do not limit such a subject matter based on the scope of Claims, but may be used in combination with technical features described in the embodiments.

In the present description, terms "first", "second", "third", "fourth", etc. are used in order to distinguish one element from another element. For example, a first element may be expressed as a second element, and the second element may be likewise expressed as the first element. This however does not depart from the scope of the presently disclosed subject matter.

Cell Culture Evaluation System (First Embodiment)

FIG. 1 illustrates a schematic configuration view of a cell culture evaluation system 1 according to an embodiment of the presently disclosed subject matter. In the embodiment, the cell culture evaluation system 1 includes measurement units 10, a first storage unit 20, a second storage unit 21, an evaluation unit 30, and an output unit 40. The first storage unit 20, the second storage unit 21, the evaluation unit 30, and the output unit 40 are or can be connected electrically or by telecommunication.

Each of the measurement units 10 includes a sensor 100 which acquires evaluation target data about motion or a state of a culture tool 70 in execution of an arbitrary culture process. In the present description, the "arbitrary culture process" means any possible process handling cells, such as a process of recovering, processing, or freezing cells or a substance (e.g. a protein, an antibody, a virus, or the like) produced by the cells, besides a cell culture process (e.g. maintained culture, extended culture, subculture, or the like). The "arbitrary culture process" is not limited particularly. The culture process which is set as an evaluation target by the cell culture evaluation system 1 according to the presently disclosed subject matter may be carried out by a person or may be carried by an automatic culture apparatus (such as a robot 80).

The cell culture evaluation system 1 according to the presently disclosed subject matter acquires evaluation target data about the motion or the state of the culture tool 70 used in execution of the culture process. The culture tool 70 evaluated by the cell culture evaluation system 1 according to the presently disclosed subject matter includes a culture container (such as a culture container of a Petri dish type, a bottle type or any shape or a storage container), and a pipette and/or a centrifuge tube. Accordingly, although not shown, at least two measurement units 10 are provided in the cell culture evaluation system 1. The pipette used in the presently disclosed subject matter is not limited particularly. Any pipette may be used as the pipette used in the presently disclosed subject matter as long as the pipette can be used for the cell culture. The centrifuge tube used in the presently disclosed subject matter is not limited particularly. Any centrifuge tube may be used as the centrifuge tube used in the presently disclosed subject matter as long as the centrifuge tube can be used in a centrifugal separator.

In the present description, each of the "evaluation target data about the motion or the state of the culture tool" and "reference data about reference motion or a reference state of the culture tool" means data about motion or a state of the culture tool, which include, for example, at least one selected from the group consisting of acceleration, angular velocity, position, posture, an operating time, the number of times of use, and temperature of the culture tool, and an amount of a liquid contained in the culture tool, dissolved oxygen (DO) in the liquid, turbidity, a discharge flowrate, a suction flowrate, and pH. That is, the "evaluation target data about the motion or the state of the culture tool" and the "reference data about the reference motion or the reference state of the culture tool" are quantifiable data expressing the motion or the state of the culture tool that can affect the state of cells. Accordingly, any sensor may be used as the sensor 100 in the measurement unit 10 as long as the sensor can acquire the aforementioned evaluation target data. For example, besides an accelerometer, a gyrosensor, a geomagnetic sensor, an impact sensor, a magnetic position sensor, a GPS sensor, a pH sensor, an optical sensor, an ultrasonic sensor, a pressure sensor, a flowrate sensor, a weight sensor, a level sensor, a proximity sensor, and a temperature sensor, known sensors can be used singly or in combination. In the presently disclosed subject matter, for example, a measurement unit described in JP-A-2013-202030 may be used as the measurement unit 10.

The first storage unit 20 can store the evaluation target data acquired by the sensor 100. The first storage unit 20 may be, for example, a memory device such as an RAM, an ROM or a flash device, a fixed disk device such as a hard disk drive, or a portable type storage medium such as a flexible disk or an optical disk, or may be a cloud server connected by telecommunication through the Internet. In a case where, for example, the first storage unit 20 is a portable type storage device, as illustrated in FIG. 1, the evaluation target data acquired by the sensor 100 are stored in the first storage unit 20, and the first storage unit 20 is connected to an arithmetic unit provided with the evaluation unit 30, for example, through a connection slot or the like so that the evaluation target data can be used for evaluation.

The second storage unit 21 stores the reference data about the reference motion or the reference state of the culture tool in execution of a referred culture process. The reference data mean data about motion or a state of the culture tool which were acquired in execution of the culture process carried out in order to manufacture a final cell product having a desired quality. The reference data also include data in a case where the final cell product having the desired quality was obtained, and data in a case where the final cell product having the desired quality was not obtained. Accordingly, the reference data may be data acquired by the measurement unit 10 of the same cell culture evaluation system 1, or may be data acquired by a measurement unit 10 of another cell culture evaluation system 1. In a manner similar to or the same as the first storage unit 20, the second storage unit 21 (and, a third storage unit, a fourth storage unit, a fifth storage unit, and a sixth storage unit which will be described later) may be, for example, a memory device such as an RAM, an ROM or a flash device, a fixed disk device such as a hard disk drive, or a portable type storage medium such as a flexible disk or an optical disk, or may be a cloud server connected by telecommunication through the Internet.

The evaluation unit 30 compares the evaluation target data stored in the first storage unit 20 with the reference data stored in the second storage unit 21 so as to evaluate the execution state of the cell culture process. The evaluation of the cell culture process by the evaluation unit 30 is performed by a processor such as a CPU or a GPU included in the evaluation unit. For example, the evaluation unit 30 can read the evaluation target data stored on a time-series basis in the first storage unit 20, and the reference data stored on a time-series basis in the second storage unit 21, compare the both with each other, and evaluate the execution of the cell culture process as abnormal at an arbitrary time point when the evaluation target data at the arbitrary time point deviates from a predetermined condition which has been set by the reference data at a corresponding time point to the arbitrary time point (see FIG. 5 (B)). In addition, the evaluation unit 30 can read the evaluation target data stored on the time-series basis in the first storage unit 20, and the reference data stored on the time-series basis in the second storage unit 21, compare the both with each other, and make an evaluation for improving work which is peculiar to a worker to lead to failure in cell manufacturing or a suggestion for the improvement when, for example, the work has been found in the cell culture process from the evaluation target data at the arbitrary time point.

Figure 6:
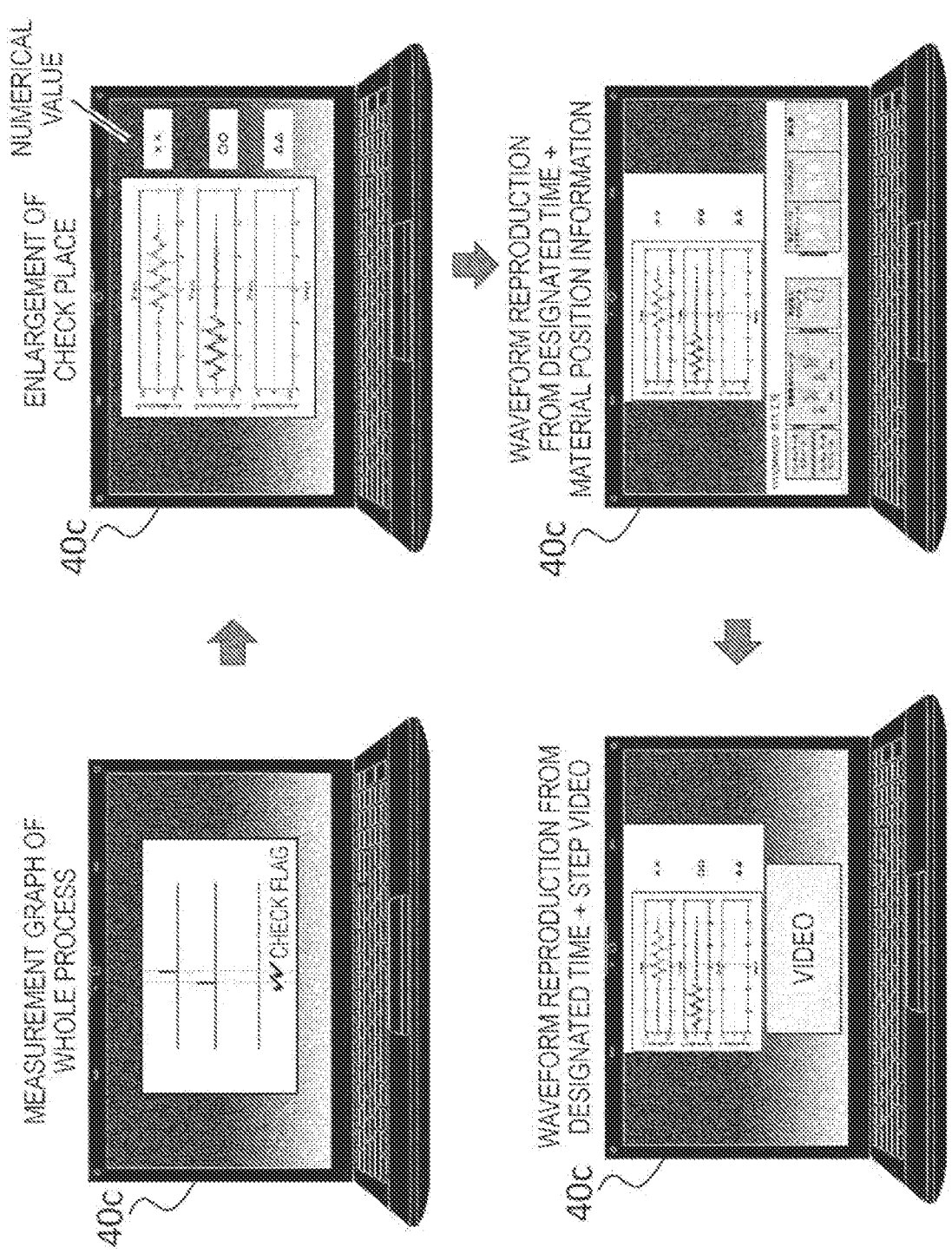
FIG. 6 illustrates examples of images displayed on the output unit of the cell culture evaluation system according to the embodiment.

The output unit 40 is configured to output an evaluation result created by the evaluation unit 30. The output unit 40 may be, for example, a monitor or a printer. Preferably, the output unit 40 is a monitor. In an embodiment, the output unit 40 is configured to output an evaluation result including information about the time point at which the abnormality occurred. In addition, in another embodiment, the output unit 40 may output the evaluation result as a time-series trend graph of the evaluation target data and the reference data (e.g. see FIGS. 5 (A) to (D) and FIG. 6). The trend graph may be enlarged or decreased by any scale factor. Thus, information about the time point when the execution of the cell culture process was determined as abnormal can be grasped in detail. In addition, in a further embodiment, the output unit 40 may output the evaluation target data and the reference data as the time-series trend graph, and display information about the time point at which the execution of the cell culture process was evaluated as abnormal on the trend graph (see FIGS. 5 (A) to (D) and FIG. 6). Thus, information about the time point at which the execution of the cell culture process was evaluated as abnormal is visually recognized easily in the cell culture evaluation system 1.

Cell Culture Evaluation System (Second Embodiment)

Figure 2:
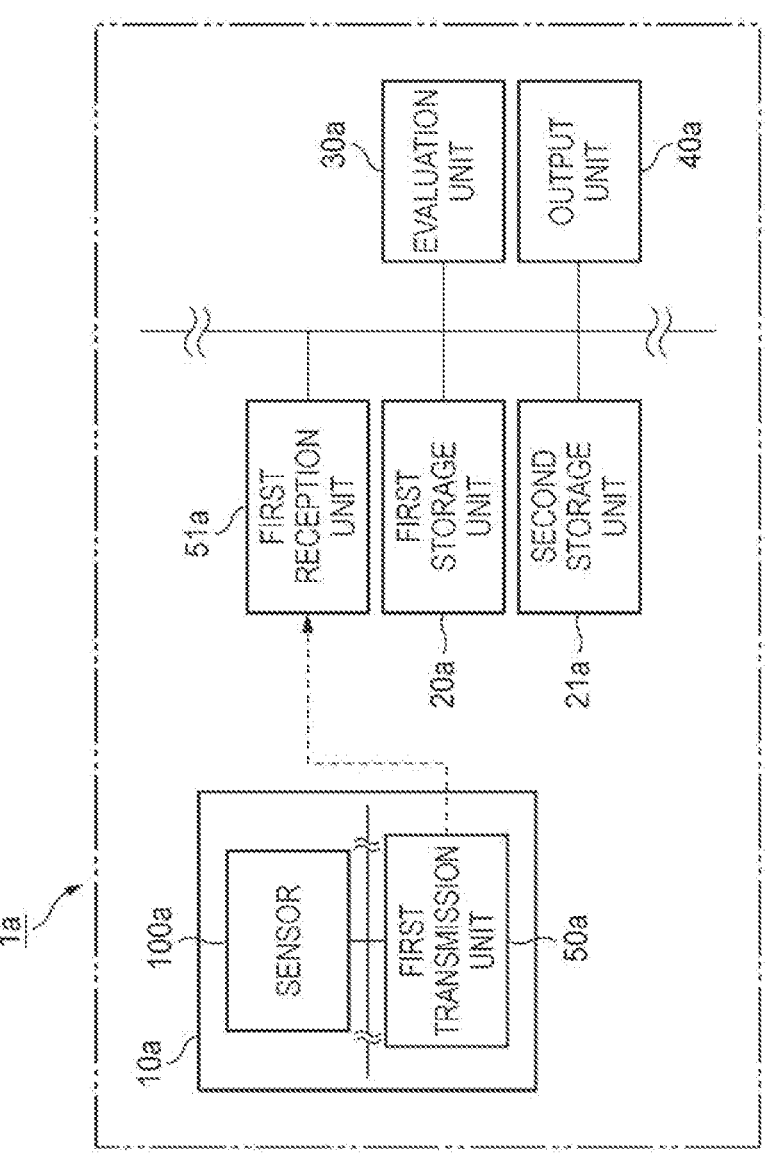
FIG. 2 is a schematic configuration view of a cell culture evaluation system according to an embodiment.

FIG. 2 illustrates a schematic configuration view of a cell culture evaluation system 1a according to an embodiment of the presently disclosed subject matter. Members of the cell culture evaluation system 1a according to the second embodiment are respectively designated by the same reference sings as those for the members provided in the cell culture evaluation system 1 according to the first embodiment except that "a" is suffixed to the reference signs of the members. The aforementioned description about the corresponding members according to the first embodiment can be applied to description about the members of the cell culture evaluation system 1a according to the second embodiment. Only members to which the description of the respective members according to the first embodiment cannot be applied will be described here. Incidentally, the culture tool 70 and the robot 80 illustrated in FIG. 1 are omitted from FIGS. 2 to 4.

In an embodiment, a measurement unit 10a of the cell culture evaluation system 1a includes a first transmission unit 50a for transmitting evaluation target data. In addition, the cell culture evaluation system 1a includes a first reception unit 51a electrically connected to a first storage unit 20a. Thus, the first storage unit 20a can receive the evaluation target data transmitted from the first transmission unit 50a through the first reception unit 51a, and store the received evaluation target data. Communication between the first transmission unit 50a and the first reception unit 51a may be wired communication, may be wireless communication, or may be communication through a portable type storage medium.

The first storage unit 20a and a second storage unit 21a may be separate storage media or may be separate regions of one and the same recording medium.

Cell Culture Evaluation System (Third Embodiment)

Figure 3:
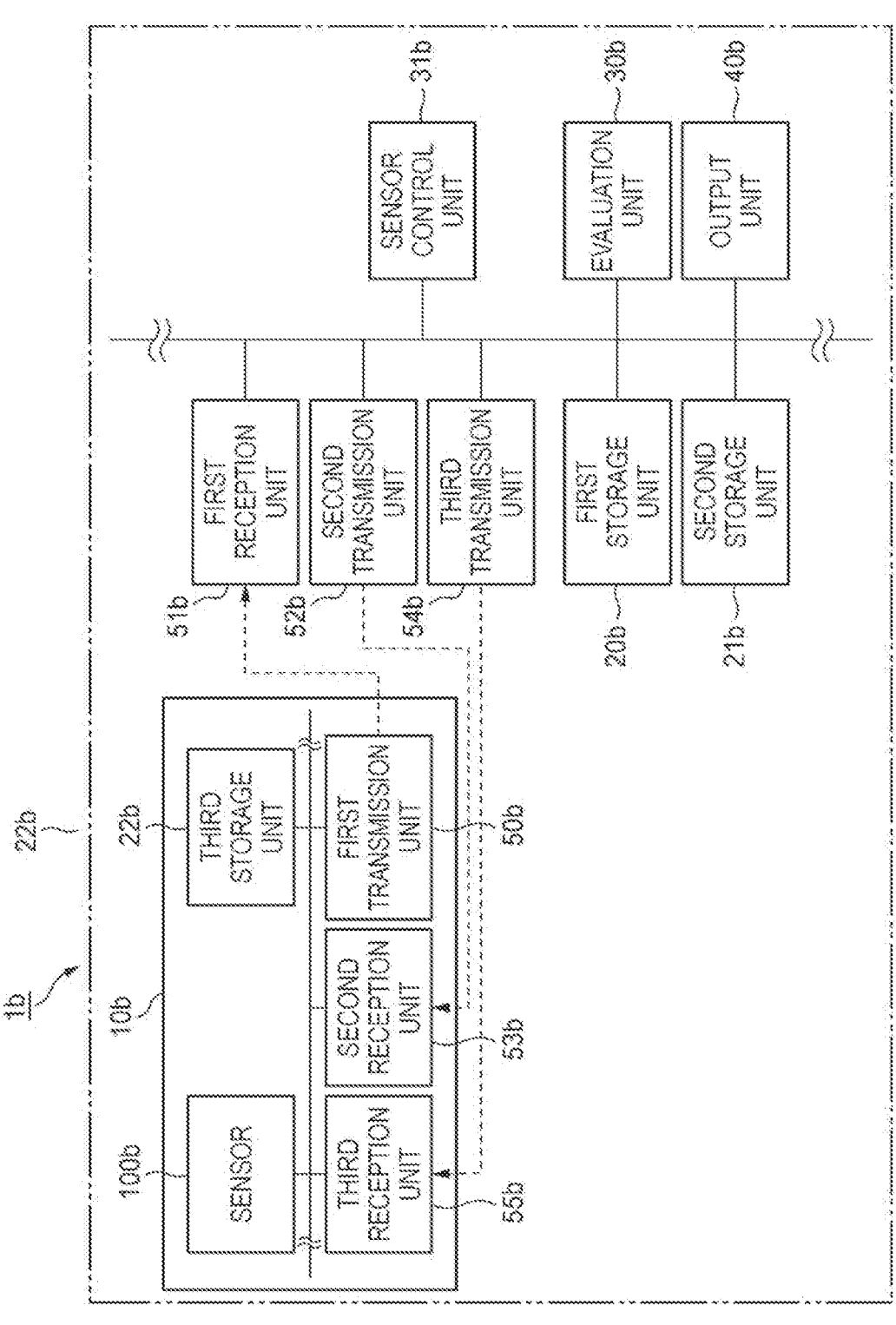
FIG. 3 is a schematic configuration view of a cell culture evaluation system according to an embodiment.

FIG. 3 illustrates a schematic configuration view of a cell culture evaluation system 1b according to an embodiment of the presently disclosed subject matter. Members of the cell culture evaluation system 1b according to the third embodiment are respectively designated by the same reference sings as those for the members provided in the cell culture evaluation system 1 according to the first embodiment and the cell culture evaluation system 1a according to the second embodiment except that "b" is suffixed to the reference signs of the members. The aforementioned description about the corresponding members according to the first embodiment and the second embodiment can be applied to description about the members of the cell culture evaluation system 1b according to the third embodiment. Only members to which the description of the respective members according to the first embodiment and the second embodiment cannot be applied will be described here.

In an embodiment, a measurement unit 10b in the cell culture evaluation system 1b may include a third storage unit 22b storing evaluation target data. Thus, in the cell culture evaluation system 1b, the evaluation target data stored in the third storage unit 22b can be transferred to a first storage unit 20b to be used.

In an embodiment, the evaluation target data temporarily stored in the third storage unit 22b may be transmitted from a first transmission unit 50b of the measurement unit 10b, received by a first reception unit 51b, transferred to the first storage unit 20b and stored in the first storage unit 20b.

In an embodiment, the cell culture evaluation system 1b may be include a sensor control unit 31b issuing an instruction for controlling start and stop of motion of the measurement unit 10b, and a second transmission unit 52b for transmitting the instruction. Further, the measurement unit 10b may include a second reception unit 53b for receiving the instruction transmitted from the second transmission unit 52b. Thus, motion of a sensor 100b of the measurement unit 10b can be started and stopped at any time.

In the embodiment, the cell culture evaluation system 1b may include a third transmission unit 54b for transmitting a parameter about a measurement condition of the motion of the sensor 100b included in the measurement unit 10b. Further, the measurement unit 10b may include a third reception unit 55b for receiving the parameter transmitted from the third transmission unit 54b. Thus, at least one of a measurement range, a period of time, and a measurement interval of the evaluation target data which can be acquired by the sensor 100b can be set.

Cell Culture Evaluation System (Fourth Embodiment)

Figure 4:
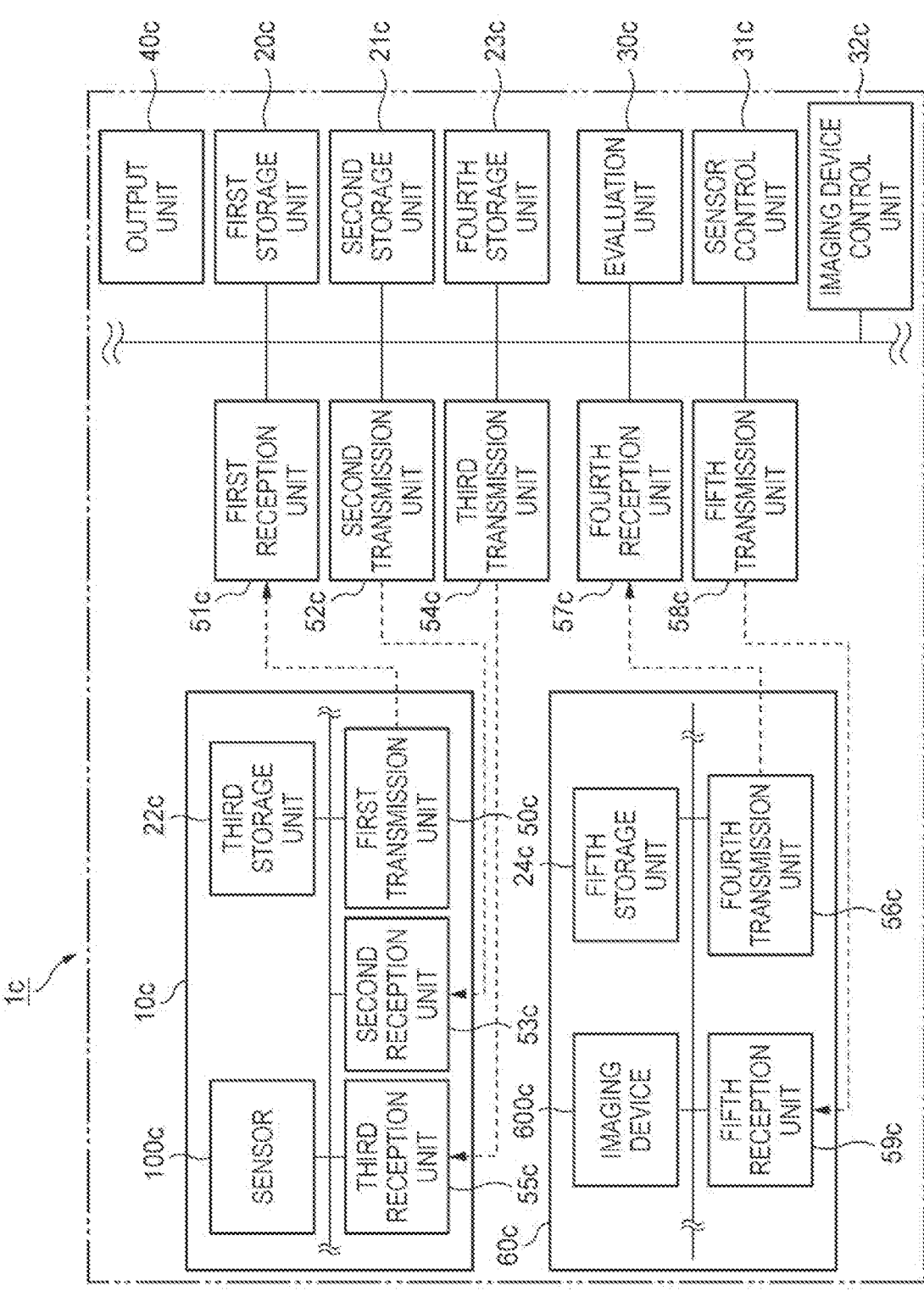
FIG. 4 is a schematic configuration view of a cell culture evaluation system according to an embodiment.

FIG. 4 illustrates a schematic configuration view of a cell culture evaluation system 1c according to an embodiment of the presently disclosed subject matter. Members of the cell culture evaluation system 1c according to the fourth embodiment are respectively designated by the same reference sings as those for the members included in the cell culture evaluation systems (1, 1a and 1b) according to the first to third embodiments except that "c" is suffixed to the reference signs of the members. The aforementioned description about the corresponding members according to the first to third embodiments can be applied to description about the members of the cell culture evaluation system 1c according to the fourth embodiment. Only members to which the description of the respective members according to the first to third embodiments cannot be applied will be described here.

In an embodiment, the cell culture evaluation system 1c may include an imaging unit 60c and a fourth storage unit 23c. In this case, the imaging unit 60c acquires an evaluation target image about motion or a state of a culture tool 70 in execution of an arbitrary culture process. A second storage unit 21c stores a reference image about reference motion or a reference state of the culture tool 70 in execution of a referred culture process. The fourth storage unit 23c stores the evaluation target image. An output unit 40c outputs the reference image and/or the evaluation target image in association with an evaluation result if occasions demand (e.g. see FIG. 6). The imaging unit 60c includes an imaging device 600c. The imaging device 600c may be a camera which can, for example, take a still image, or may be a video camera which can take video. Preferably, the imaging device 600c is a video camera. When the imaging device 600c is the video camera, abnormality of the motion executed in the culture process at a time point at which the motion was determined as abnormal by the cell culture evaluation system 1c can be visually recognized in more detail.

In an embodiment, the imaging unit 60c may include a fifth storage unit 24c storing the evaluation target image. Thus, in the cell culture evaluation system 1c, the evaluation target image stored in the fifth storage unit 24c can be transferred to the fourth storage unit 23c to be used.

In an embodiment, the evaluation target image temporarily stored in the fifth storage unit 24c may be transmitted from a fourth transmission unit 56c of the imaging unit 60c, received by a fourth reception unit 57c, transferred to the fourth storage unit 23c, and stored in the fourth storage unit 23c.

In an embodiment, the imaging unit 60c may not include the fifth storage unit 24c, and the evaluation target image may be transmitted from the fourth transmission unit 56c, received by the fourth reception unit 57c, transferred to the fourth storage unit 23c, and stored in the fourth storage unit 23c.

In an embodiment, the cell culture evaluation system 1c may include an imaging device control unit 32c issuing an instruction for controlling start and stop of operation of the imaging unit 60c, and a fifth transmission unit 58c for transmitting the instruction. Further, the imaging unit 60c may include a fifth reception unit 59c for receiving the instruction transmitted from the fifth transmission unit 58c. Thus, the operation of the imaging device 600c of the imaging unit 60c can be started and stopped at any time.

In the embodiment, the fourth storage unit 23c may be a portable type storage device. In this case, the evaluation target image acquired by the imaging device 600c of the imaging unit 60c is stored in the fourth storage unit 23c, and the fourth storage unit 23c is connected to an arithmetic unit provided with an evaluation unit 30c, for example, through a connection slot etc. so that the evaluation target image can be used for evaluation (not shown).

In an embodiment, the second storage unit 21c in the cell culture evaluation system 1c may store the layout of culture tools 70 and culture materials (e.g. culture medium bolts, pipettes, culture containers, centrifuge tubes, etc.) on a time-series basis in execution of a referred culture process (e.g. see FIG. 5 (D)). In this case, the output unit 40c can output an evaluation result associated with the layout (FIGS. 5 (A) to (D) and FIG. 6).

In the present description, the transmission units (the first to fifth transmission units) and the reception units (the first to fifth reception units) are described as separate elements for convenience of explanation. However, it should be noted that they may be bidirectional "communication units" in each of which the transmission unit and the reception unit are integrated, or one transmission unit or one reception unit may be shared among them.

The invention claimed is:

1. A cell culture evaluation system comprising a measurement unit, a first storage unit, a second storage unit, an evaluation unit, and an output unit, wherein:
   the measurement unit includes a sensor that acquires evaluation target data about motion or a state of a culture tool in execution of an arbitrary culture process;
   the first storage unit is configured to store the evaluation target data acquired by the measurement unit;
   the second storage unit is configured to store reference data about reference motion or a reference state of the culture tool in execution of a referred culture process;
   the evaluation unit is configured to:
      compare the evaluation target data stored in the first storage unit with the reference data stored in the second storage unit; and
      evaluate an execution state of a cell culture process based on the comparison to assure the quality of a final cell product;
   the output unit outputs an evaluation result created by the evaluation unit; and
   the culture tool includes a culture container, and a pipette and/or a centrifuge tube.

2. The cell culture evaluation system according to claim 1, wherein:
   each of the evaluation target data and the reference data include at least one selected from the group consisting of acceleration, angular velocity, position, posture, an operating time, the number of times of use, and temperature of the culture tool, and an amount of a liquid contained in the culture tool, dissolved oxygen (DO) in the liquid, turbidity, a discharge flowrate, a suction flowrate and pH.

3. The cell culture evaluation system according to claim 1, wherein:
   the evaluation unit compares the evaluation target data stored in the first storage unit with the reference data stored in the second storage unit, and evaluates the execution of the cell culture process as abnormal at an arbitrary time point when the evaluation target data at the arbitrary time point deviate from a predetermined condition set by the reference data at a corresponding time point to the arbitrary time point; and
   the output unit outputs an evaluation result including information about the time point at which the abnormality occurred.

4. The cell culture evaluation system according to claim 3, wherein:
   the output unit outputs the evaluation target data and the reference data as a time-series trend graph, and displays the information about the time point at which the execution of the cell culture process was evaluated as abnormal on the trend graph.

5. The cell culture evaluation system according to claim 1, wherein:
   the output unit outputs the evaluation result as a time-series trend graph of the evaluation target data and the reference data.

6. The cell culture evaluation system according to claim 5, wherein:
   the trend graph can be enlarged and decreased by a scale factor.

7. The cell culture evaluation system according to claim 1, wherein:
   the measurement unit includes a third storage unit that stores the evaluation target data, and the evaluation target data stored in the third storage unit are transferred to the first storage unit to be used.

8. The cell culture evaluation system according to claim 7, wherein:

the measurement unit includes a first transmission unit that transmits the evaluation target data; and the first storage unit receives the evaluation target data transmitted from the first transmission unit through a first reception unit, and stores the received evaluation target data.

9. The cell culture evaluation system according to claim 5, wherein:

the cell culture evaluation system further comprises a sensor control unit that issues an instruction for controlling start and stop of motion of the measurement unit, and a second transmission unit that transmits the instruction; and the measurement unit further includes a second reception unit that receives the instruction transmitted from the second transmission unit.

10. The cell culture evaluation system according to claim 9, wherein:

the cell culture evaluation system further comprises a third transmission unit that transmits a parameter about a measurement condition of motion of a sensor included in the measurement unit; and the measurement unit further includes a third reception unit that receives the parameter transmitted from the third transmission unit.

11. The cell culture evaluation system according to claim 10, further comprising an imaging unit and a fourth storage unit, wherein:

the imaging unit acquires an evaluation target image about motion or a state of the culture tool in execution of the arbitrary culture process;

the second storage unit stores a reference image about the reference motion or the reference state of the culture tool in execution of the referred culture process;

the fourth storage unit stores the evaluation target image; and the output unit outputs the reference image and/or the evaluation target image in association with the evaluation result if occasions demand.

12. The cell culture evaluation system according to claim 11, wherein:

the imaging unit includes a fifth storage unit that stores the evaluation target image, and the evaluation target image stored in the fifth storage unit is transferred to the fourth storage unit to be used.

13. The cell culture evaluation system according to claim 11, wherein:

the fourth storage unit is a portable type storage device.

14. The cell culture evaluation system according to claim 11, wherein:

the imaging unit includes a fourth transmission unit that transmits the evaluation target image; and the fourth storage unit receives the evaluation target image transmitted from the fourth transmission unit through a fourth reception unit, and stores the received evaluation target image.

15. The cell culture evaluation system according to claim 1, wherein:

the first storage unit is a portable type storage device.

16. The cell culture evaluation system according to claim 1, wherein:

the cell culture evaluation system evaluates a culture process carried out by a person or an automatic culture apparatus.

17. The cell culture evaluation system according to claim 1, wherein:

the second storage unit stores a layout of the culture tool and a culture material on a time-series basis in execution of the referred culture process; and the output unit outputs the evaluation result associated with the layout.

\* \* \* \* \*